(12) United States Patent
Han et al.

(10) Patent No.: US 8,734,911 B2
(45) Date of Patent: May 27, 2014

(54) NANOCOUPLING FOR IMPROVEMENT OF COATING ADHESION OF POLYMER ON METAL SUBSTRATES

(75) Inventors: Dong Keun Han, Seoul (KR); Kwi Deok Park, Seoul (KR); Jae-Jin Kim, Seoul (KR); Chul Ho Park, Seoul (KR); Seong Bae Cho, Seoul (KR)

(73) Assignee: Korea Institute of Science and Technology (KR)

( * ) Notice: Subject to any disclaimer, the term of this patent is extended or adjusted under 35 U.S.C. 154(b) by 351 days.

(21) Appl. No.: 12/912,913

(22) Filed: Oct. 27, 2010

(65) Prior Publication Data

US 2011/0111367 A1 May 12, 2011

(30) Foreign Application Priority Data

Nov. 10, 2009 (KR) .................. 10-2009-0108221

(51) Int. Cl.
*B05D 3/06* (2006.01)
*B05D 3/08* (2006.01)
*H05H 1/00* (2006.01)

(52) U.S. Cl.
USPC ............ 427/535; 427/2.1; 427/532; 427/533; 427/539

(58) Field of Classification Search
USPC ........ 427/2.1, 2.24, 2.25, 327, 532, 533, 535, 427/551, 539
See application file for complete search history.

(56) References Cited

U.S. PATENT DOCUMENTS

| | | | |
|---|---|---|---|
| 6,248,127 B1 * | 6/2001 | Shah et al. | 623/1.15 |
| 6,464,889 B1 | 10/2002 | Lee et al. | |
| 6,599,558 B1 * | 7/2003 | Al-Lamee et al. | 427/2.24 |
| 2007/0071879 A1 * | 3/2007 | Rypacek et al. | 427/2.1 |

FOREIGN PATENT DOCUMENTS

| | | |
|---|---|---|
| JP | 2007-260247 | 10/2007 |
| KR | 100892866 | 4/2009 |
| WO | WO 2006008739 A2 * | 1/2006 |

OTHER PUBLICATIONS

Hsu et al. Improved cell adhesion by plasma-induced grafting of L-lactide onto polyurethane surface. Biomaterials 21 (2000) 359}367.*
Albertsson et al. Recent Developments in Ring Opening Polymerization of Lactones for Biomedical Applications. Biomacromolecules 2003, 4, 1466-1486.*
Surface-initiated, ring-opening polymerization of p-dioxanone from gold and silicon oxide surfaces, Kuk Ro Yoon,et.al., The Royal Society of Chemistry 2003, J. Mater. Chem, 2003, 13, 2910-2914.
Biomimetic Anchor for Surface-Initiated Polymerization from metal substrates,Xiaowa Fan, et.al., JACS Articles, J. Am. Chem. Soc. 2005, 127, 15843-15847.
High lubricious surface of cobalt-chromium-molybdenum alloy prepared by grafting poly (2-methacryoyloxyethyl, phosphorylcholine), Mazayuki Kyomoto, et.al., Elsevier Ltd., Biomaterials 28 (2007) 3121-3130.
Antibacterial Inorganic-Organic Hybrid Coatings on Stainless Steel via Consecutive Surface Initiated Atom Transfer Radical Polymerization for Biocorrosion Prevention, S.J.Yuan, et.al., Langmuir Article 2010, 26(9), 6728-6736.

* cited by examiner

*Primary Examiner* — Cachet Sellman
(74) *Attorney, Agent, or Firm* — Ostrolenk Faber LLP

(57) ABSTRACT

Disclosed is nanocoupling of a polymer onto a surface of a metal substrate for improving coating adhesion of the polymer on the metal substrate, and in vivo stability and durability of the polymer. In accordance with the present invention, the polymers can be grafted via a chemical bonding on the surface of the metal substrate by the nanocoupling, by which adhesion, biocompatibility and durability of a polymer-coated layer which is to be formed later on the metal substrate were remarkably improved; therefore, the nanocoupling according to the present invention can be applied to surface modification of a metal implant, such as stents, mechanical valves, and an articular, a spinal, a dental and an orthopedic implants.

7 Claims, No Drawings

NANOCOUPLING FOR IMPROVEMENT OF COATING ADHESION OF POLYMER ON METAL SUBSTRATES

BACKGROUND OF THE INVENTION

1. Field of the Invention

The present invention relates to nanocoupling of a polymer onto a surface of a metal substrate for improving coating adhesion of the polymer onto the surface of the metal substrate, and in vivo stability and durability of the polymer.

2. Background of the Invention

Recently, aging of a population gives rise to rapid increase in use of metal implants or the like. The metal implants have been used as materials for stents in vascular and nonvascular systems, mechanical valves, and an articular, a spinal, a dental and an orthopedic implants, and the like. However, the metal implant may cause an accurate closure due to thrombosis after surgical operation. The metal implant may also act as a traumatic element onto endothelium to result in an neointima proliferation, which may cause restenosis, inflammatory response and the like, and even cause tissue necrosis in serious cases.

Surface modification for rendering biocompatibility to the metal implants enhances biocompatibility while maintaining superior mechanical properties of the metal. A representative of the metal surface modification method is a chemical surface treatment. However, the chemical surface treatment may cause the metal surface to be rough, and also may decrease biocompatibility due to use of a toxic material in vivo.

Another surface modification method is to coat a biodegradable polymer onto a surface of a metal implant. Here, a typically used biodegradable polymer may include polyglycolic acid (PGA), poly-L-lactic acid (PLLA), poly-D,L-lactic acid (PDLLA), polylactic-co-glycolic acid (PLGA), poly-$\epsilon$-carprolactone (PCL), polyaminoic acid, polyanhydride (PA), polyorthoester (POE), or copolymers thereof. However, in case of coating the biodegradable polymer through an air spray or ultrasonic coating, the coated polymer is separated from the surface of the metal implant within a short time, and accordingly, the metal implant is exposed to blood and tissue cells, which may cause several problems, such as restenosis, blood coagulation, drug release within a short period of time, high cytotoxicity, decrease of cell adhesion, inflammatory response inevitably accompanied with infiltration of bacteria and the like. Therefore, improvement of the coating adhesion of the biodegradable polymers coated on the metal implant is recognized as a very important factor for improving the function of the metal implant.

SUMMARY OF THE INVENTION

Therefore, to address the related art problems, an object of the present invention is to provide nanocoupling for chemically coupling a polymer onto a metal surface, so as to improve coating adhesion, in vivo stability (biocompatibility) and durability of the polymer on the surface of metal substrate.

The object of the present invention can be achieved by the followings:

(1) A method for fabricating a surface-modified metal substrate, comprising (a) introducing hydroxyl groups on a surface of a metal substrate, and (b) polymerizing a monomer on the hydroxyl group-introduced surface of the metal substrate, so as to make a polymer generated from the polymerization of the monomer chemically bonded onto the surface of the metal substrate through oxygen atoms.

(2) The fabrication method of (1) above, further comprising (c) coating a polymer, which is the same as or different from the polymer generated from the polymerization of the monomer, onto the surface of the substrate obtained in step (b).

(3) A surface-modified metal substrate, comprising (a) a metal substrate, and (b) a polymer layer chemically coupled onto the surface of the metal substrate through oxygen atoms.

(4) The surface-modified metal substrate of (3) above, further comprising (c) a polymer-coated layer on the polymer layer (b), wherein the polymer of the polymer-coated layer (c) is the same as or different from the polymer of the polymer layer (b).

(5) A method for modifying a surface of a metal substrate or improving coating adhesion of a polymer onto the surface of the metal substrate, comprising polymerizing a monomer on a hydroxyl group-introduced surface of the metal substrate, so as to make a polymer generated from the polymerization of the monomer chemically coupled onto the surface of the metal substrate through oxygen atoms.

The present invention has provided a surface-modified metal substrate having superior biocompatibility, in vivo stability and durability, a fabrication method thereof, and a method for improving the biocompatibility, durability and adhesion of a polymer to the metal substrate.

In accordance with the present invention, an appropriate selection of a nanocoupling material for the surface of a metal substrate makes it possible to control biocompatibility and mechanical properties. Therefore, through surface modification of various metal substrates, the nanocoupling according to the present invention can render new functions to metal products, and makes it possible to fabricate higher value-added metal products, and to achieve reduction of fabrication costs by virtue of a simple process.

The foregoing and other objects, features, aspects and advantages of the present invention will become more apparent from the following detailed description of the present invention when taken in conjunction with the accompanying drawings.

DETAILED DESCRIPTION OF THE INVENTION

The present invention relates to a method for fabricating a surface-modified metal substrate, comprising (a) introducing hydroxyl group on a surface of a metal substrate, and (b) polymerizing a monomer on the hydroxyl group-introduced surface of the metal substrate, so as to make a polymer generated from the polymerization of the monomer chemically coupled onto the surface of the metal substrate through oxygen atoms.

In step (a), the surface of the metal substrate is activated, and hydroxyl group is introduced on the surface of the metal substrate.

The metal substrate may include a stent for a vascular and nonvascular system, a mechanical valve, and an articular, a spinal, a dental and an orthopedic implants, and the like. The metal may be selected from the group consisting of stainless steel, cobalt-chromium (Co—Cr), titanium (Ti), nitinol, gold (Au), silver (Ag), platinum (Pt), tantalum (Ta), magnesium (Mg), and a metal alloy consisting of two or more metals as mentioned above.

In step (a), the surface of the metal substrate is activated through a physical or chemical method, thereby introducing hydroxyl group (—OH) on the surface of the metal substrate.

The physical method may include plasma or ion beam treatment using at least one gas selected from the group consisting of argon, nitrogen, oxygen, steam, ammonia and tetrafluoromethane. Upon the plasma or ion beam treatment, a voltage may be in the range of 500 V to 100 kV, preferably, in the range of 1 kV to 100 kV, power may be in the range of 50 W to 10 kW, preferably, in the range of 50 W to 200 W, and time may be in the range of 1 second to 1 hour, preferably, in the range of 10 seconds to 10 minutes.

The chemical method may include a treatment of the surface of the metal substrate with a base or an acid. Preferably, in the chemical method, the metal substrate is dipped in an alkaline solution in pH 9 to 12. Here, temperature may be in the range of from room temperature to 150° C., preferably, in the range of from 60° C. to 100° C. The base may be at least one selected from the group consisting of aqueous ammonia, sodium hydroxide, potassium hydroxide, lithium hydroxide and calcium hydroxide, wherein the alkaline solution may be used in admixture with hydrogen peroxide.

In step (b), a monomer, preferably, a monomer which generate a biocompatible and biodegradable polymer through polymerization, is polymerized on the hydroxyl group-introduced surface of the metal substrate, so as to make the polymer generated from the polymerization of the monomer chemically coupled onto the surface of the metal substrate through oxygen atoms.

The monomer may be a monomer containing a ring structure, for example, at least one selected from the group consisting of glycolide, L-lactide, D-lactide, D,L-lactide, ε-caprolactone, trimethylene carbonate and p-dioxanone. Here, the polymer, which is generated through a ring-opening polymerization of the monomer, is chemically coupled onto the surface of the metal substrate through oxygen atoms. The monomer containing a ring structure is used such that the amount of polymer generated from the polymerization of the monomer is to be 0.001 to 50 g/cm$^2$, preferably, 0.1 to 10 g/cm$^2$ with respect to the surface area of the metal substrate.

A catalyst for the ring-opening polymerization of the monomer is used in an amount of from 0.0001 to 0.1% by weight, preferably, 0.0002 to 0.01% by weight of the monomer, and the polymerization is carried out at room temperature to 200° C., preferably, at 40 to 90° C. The catalyst for the ring-opening polymerization of the monomer containing a ring structure may include Tin(II) octoate or dibutyltin dilaurate.

In step (b), a monomer containing a carboxylic acid group (—COOH) which is not a ring structure, for example, at least one selected from the group consisting of glycolic acid, L-lactic acid, D-lactic acid, D,L-lactic acid and caprolactic acid may be used. In this case, a polymer, which is generated through dehydration-polymerization of the monomer, is chemically coupled onto the surface of the metal substrate through oxygen atoms.

The monomer containing a carboxylic acid group is used such that the amount of polymer generated from the polymerization of the monomer is to be 0.001 to 50 g/cm$^2$, preferably, 0.1 to 10 g/cm$^2$ with respect to the surface area of the metal substrate.

A catalyst for the dehydration-polymerization of the monomer containing a carboxylic acid group is used in an amount of from 0.0001 to 0.1% by weight, preferably, 0.0002 to 0.01% by weight of the monomer. The polymerization is carried out at room temperature to 200° C., preferably, at 60 to 150° C.

The catalyst for the dehydration-polymerization of the monomer containing a carboxylic acid group may include hafnium(IV) salts selected from HfCl$_4$.(THF)$_2$ and Hf(O-tOBu)$_4$, and scandium trifluoromethanesulfonate (Sc(OTF)$_3$).

The polymerization in step (b) may be a surface polymerization in solution. A solvent for the polymerization may be at least one selected from the group consisting of toluene, chloroform, methylene chloride, tetrahydrofuran, dioxane, benzene, xylene, acetonitrile and carbon tetrachloride. Herein, the monomer is used in an amount of 0.1 to 90 weight part for 100 weight part of the solvent for the polymerization.

The method for fabricating the surface-modified metal substrate according to the present invention may further comprise, after step (b), (c) coating a polymer, which is the same as or different from the polymer generated from the polymerization of the monomer, onto the surface of the substrate obtained in step (b).

The polymer used in step (c) may be the same as or different from the polymer generated from the polymerization of the monomer in step (b). For instance, the polymer to be used in step (c) may be at least one selected from the group consisting of polyglycolic acid (PGA), poly-L-lactic acid (PLLA), poly-D,L-lactic acid (PDLLA), polylactic-co-glycolic acid (PLGA), poly-ε-carprolactone (PCL), poly(trimethylene carbonate), poly-p-dioxanone, polyaminoic acid, polyanhydride (PA), polyorthoester (POE), and any copolymer thereof.

In step (c), the polymer is coated by at least one method selected from the group consisting of mechanical coating, gas spray coating, dipping, polarized coating, electrostatic coating, ultrasonic coating and electrospray coating.

In one detailed embodiment according to the present invention, a biodegradable polymer is coated by dipping. In this case, the surface-modified metal substrate fabricated in step (b) is dipped in a solution obtained by dissolving the polymer in an organic solvent. Here, the organic solvent may be any solvent in which the biodegradable polymer can be dissolved. Particular examples of the organic solvent may include, but not limited to, acetone, dioxane, acetonitrile, chloroform, methylene chloride, tetrahydrofuran, toluene, xylene, benzene, or any combination thereof. The concentration of the biodegradable polymer solution may be 0.01 to 90% by weight, preferably, 0.01 to 30% by weight.

The present invention also relates to a surface-modified metal substrate, comprising (a) a metal substrate, and (b) a polymer layer chemically coupled onto the surface of the metal substrate through oxygen atoms.

The metal substrate may be a stent for a vascular and nonvascular system, a mechanical valve, and an articular, a spinal, a dental and an orthopedic implants, and the like. The metal may be selected from the group consisting of stainless steel, cobalt-chromium (Co—Cr), titanium (Ti), nitinol, gold (Au), silver (Ag), platinum (Pt), tantalum (Ta), magnesium (Mg) and any metal alloy composed of two or more metals as mentioned above.

The polymer consisting of the polymer layer of step (b) may be at least one selected from the group consisting of polyglycolic acid (PGA), poly-L-lactic acid (PLLA), poly-D, L-lactic acid (PDLLA), polylactic-co-glycolic acid (PLGA), poly-ε-carprolactone (PCL), poly(trimethylene carbonate), poly-p-dioxanone, polyaminoic acid, polyanhydride (PA), polyorthoester (POE), and any copolymer thereof.

The surface-modified metal substrate according to the present invention may further comprise (c) a polymer-coated layer on the polymer layer (b), wherein the polymer of the polymer-coated layer (c) is the same as or different from the polymer of the polymer layer (b).

The polymer consisting of the polymer-coated layer (c) may be the same as or different from the polymer consisting of the polymer layer (b). In particular, the polymer consisting of the polymer-coated layer (c) may be at least one selected from the group consisting of polyglycolic acid (PGA), poly-L-lactic acid (PLLA), poly-D,L-lactic acid (PDLLA), poly-lactic-co-glycolic acid (PLGA), poly-ε-carprolactone (PCL), poly(trimethylene carbonate), poly-p-dioxanone, polyaminoic acid, polyanhydride (PA), polyorthoester (POE), and any copolymer thereof.

The method for fabricating a surface-modified metal substrate according to the present invention may be applied for modifying the surface of a metal substrate or improving coating adhesion of a polymer onto the surface of the metal substrate. Hence, the present invention also relates to a method for modifying a surface of a metal substrate or for improving coating adhesion of a polymer onto the surface of the metal substrate, wherein the method comprises polymerizing a monomer on a hydroxyl group-introduced surface of the metal substrate, so as to make a polymer generated from the polymerization of the monomer chemically coupled onto the surface of the metal substrate through oxygen atoms.

Here, the metal substrate may be any metal substrate as long as hydroxyl groups can be introduced onto its surface. However, if the metal substrate is a metal implant, it is required that the metal be appropriate to be used in vivo, for example, at least one selected from the group consisting of stainless steel, cobalt-chromium (Co—Cr), titanium (Ti), nitinol, gold (Au), silver (Ag), platinum (Pt), tantalum (Ta), magnesium (Mg) and any metal alloy composed of two or more metals as mentioned above.

The monomer may also be any type as long as it can be polymerized on the surface of the metal substrate through hydroxyl groups which are introduced on the surface of the metal substrate. Preferably, the monomer may be one which may form a biocompatible and biodegradable polymer through polymerization, in particular, at least one selected from the group consisting of glycolide, L-lactide, D-lactide, D,L-lactide, ε-caprolactone, trimethylene carbonate, p-dioxanone, glycolic acid, lactic acid and caprolactic acid.

In the method for modifying a surface of a metal substrate or improving coating adhesion of a polymer onto the surface of the metal substrate, detailed procedures are the same as those described in the method for fabricating the surface-modified metal substrate.

EXAMPLES

Hereinafter, the detailed description of the present invention will be given through the following examples. However, those examples are merely illustrative, and may not be understood as limiting the scope of the present invention.

Example 1

A stainless steel metal substrate was dipped in acetone, and washed for 1 to 10 minutes using ultrasounds. Afterwards, the dried metal substrate was put into a plasma chamber, treated with plasma while supplying therein oxygen gas under 1.33 Pa and 50 W for 10 minutes. The plasma-treated metal substrate was activated in the air for about 30 minutes, so as to make hydroxyl group introduced on the surface of the metal substrate.

The metal substrate, on the surface of which hydroxyl groups are introduced, was then put into lactide (1 g) in toluene (10 ml), to which Tin(II) octoate as a catalyst was added in a weight ratio of 1/5000 with respect to the lactide. Polymerization was then carried out with maintaining a temperature at 40 to 90° C. Unreacted monomer and polymer which was not coupled onto the surface of the metal substrate were removed using toluene and chloroform.

The surface of the resulting surface-modified metal substrate was then coated by electrospraying with a solution in which PLLA as a biodegradable polymer was dissolved in chloroform at the concentration of 0.5% by weight.

Example 2

A dried cobalt-chrome (Co—Cr) metal substrate was dipped in a solution in which aqueous ammonia, hydrogen peroxide and distilled water were mixed in the ratio of 1:1:5 (by volume), and then subjected to an oxidization for 5 minutes at 80° C. The metal substrate was then washed several times with distilled water and ethanol to activate the metal substrate surface, thereafter polymerization was carried out on the surface of the metal substrate using glycolide as a monomer.

The surface of the resulting surface-modified metal substrate was then coated with a solution in which PGA as a biodegradable polymer was dissolved in hexafluoroisopropyl alcohol, in the same method as described in Example 1.

Example 3

A surface of a titanium (Ti) metal substrate was activated, and polymerization was carried out on the surface of the metal substrate using ε-carprolactone as a monomer, by the same method as described in Example 1.

The surface of the resulting surface-modified metal substrate was coated with a solution, obtained by dissolving PCL as a biodegradable polymer in methylene chloride, in the same method as described in Example 1.

Example 4

A nitinol metal substrate was oxidized according to the method described in Example 2 to activate its surface.

The surface of the metal substrate was then modified using glycolide and lactide as monomers in a ratio of 1:1 by weight, according to the method as described in Example 1.

The surface of the resulting surface-modified metal substrate was coated with a solution, obtained by dissolving PLGA as a biodegradable polymer in acetone, in the same method as described in Example 1.

Example 5

A surface of a stainless steel metal substrate was activated according to the same method as described in Example 1, and then modified using lactide and ε-carprolactone as monomers in a weight ratio of 1:1.

The surface of the resulting surface-modified metal substrate was coated with a solution, obtained by dissolving poly(lactic acid)-carprolactone block copolymer (PLCL) as a biodegradable polymer in chloroform, in the same method as described in Example 1.

Example 6

A surface of a tantalum metal substrate was activated according to the same method as described in Example 1. Dehydration polymerization was then carried out using lactic acid as a monomer and adding $HfCl_4 \cdot (THF)_2$ as a catalyst in a weight ratio of 1/5000 with respect to the monomer.

The surface of the resulting surface-modified metal substrate was coated with a solution, obtained by dissolving PLLA as a biodegradable polymer in chloroform, in the same method as described in Example 1.

Comparative Example 1

PLLA as a biodegradable polymer was dissolved in chloroform, and a surface of a stainless steel metal substrate, of which surface was not modified, was coated with the resulting solution, according to the same method as described in Example 1.

Evaluation of Adhesion and Durability

Adhesion (N/mm$^2$) of the polymer coated on each surface-modified metal substrate in Examples 1 to 6 and Comparative Example 1 was measured with Universal Testing Machine. The measurement was conducted at 10 mm/min with a sample size of 1×1 cm$^2$.

Each of the surface-modified metal substrate was coated with a polymer, and then put into a tube with a diameter of 3 mm. At a flow rate of 250 ml/min, the time taken for the complete removal of the coated polymer layer was measured, and the measured value was regarded as a durability value of the coated biodegradable polymer.

Adhesions and durabilities measured through the above procedures, of the polymer on the surface-modified metal substrates, which were fabricated in Examples 1 to 6 and Comparative Example 1, were shown in Table 1 as follows.

| Sample | Adhesion (N/mm$^2$) | Durability (day) |
|---|---|---|
| Example 1 | 127 ± 7 | >120 ± 11 |
| Example 2 | 119 ± 8 | >70 ± 6 |
| Example 3 | 113 ± 4 | >92 ± 5 |
| Example 4 | 102 ± 5 | >62 ± 8 |
| Example 5 | 113 ± 6 | >82 ± 3 |
| Example 6 | 125 ± 8 | >110 ± 9 |
| Comparative Example 1 | 17 ± 4 | 3 ± 1 |

As shown in Table 1, when a polymer was coated on a non-modified surface of a metal substrate in Comparative Example 1, the adhesion and the durability of the polymer layer on the metal substrate surface were remarkably low. When the surface of a metal substrate was modified according to Examples 1 to 6 and then coated with a polymer, the types of metal substrates did not drastically affect on the adhesion of the polymer layers, but it was observed that the durability was relatively low for PGA or PLGA since the durability depends on the rate of degradation of biocompatible polymers.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A method for fabricating a surface-modified metal substrate, comprising:
   (a) introducing hydroxyl groups on a surface of a metal substrate through an activation of the surface by plasma or ion beam treatment using gas which includes oxygen, under conditions of voltage of 1 kV to 100 kV, power of 50 W to 200 W and for a time of 10 seconds to 10 minutes; and
   (b) polymerizing a monomer on the hydroxyl group-introduced surface of the metal substrate with an amount of 0.001 to 50 g/cm$^2$ relative to surface area of the metal substrate, so as to make a polymer,
   wherein the monomer is chemically and directly coupled onto the surface of the metal substrate through oxygen atoms, and the polymerization is generated through a ring-opening polymerization or dehydration-polymerization of the monomer with a catalyst.

2. The method according to claim 1, wherein the metal is at least one selected from the group consisting of stainless steel, cobalt-chromium, titanium, nitinol, gold, silver, platinum, tantalum, magnesium, and a metal alloy composed of two or more metals as mentioned above.

3. The method according to claim 1, wherein the metal substrate is selected from the group consisting of a stent for a vascular stent, a nonvascular system, a mechanical valve, an articular implant, a spinal implant, a dental implant and an orthopedic implant.

4. The method according to claim 1, wherein the monomer is at least one selected from the group consisting of glycolide, L-lactide, D-lactide, D,L-lactide, ε-caprolactone, trimethylene carbonate, p-dioxanone, glycolic acid, lactic acid and caprolactic acid.

5. The method according to claim 1, further comprising (c) coating a polymer, which is the same as or different from the polymer generated from the polymerization of the monomer, onto the surface of the substrate obtained in step (b).

6. The method according to claim 5, wherein the polymer coated in step (c) is at least one selected from the group consisting of polyglycolic acid, poly-L-lactic acid, poly-D,L-lactic acid, polylactic-co-glycolic acid, poly-ε-carprolactone, poly(trimethylene carbonate), poly-p-dioxanone, polyaminoic acid, polyanhydride, polyorthoester, and copolymers thereof.

7. A method for modifying a surface of a metal substrate or improving coating adhesion of a polymer onto the surface of the metal substrate, comprising:
   (a) introducing hydroxyl groups on a surface of a metal substrate through an activation of the surface by plasma or ion beam treatment using gas which includes oxygen, under conditions of voltage of 1 kV to 100 kV, power of 50 W to 200 W and for a time of 10 seconds to 10 minutes; and
   (b) polymerizing a monomer on the hydroxyl group-introduced surface of the metal substrate with an amount of 0.001 to 50 g/cm$^2$ relative to surface area of the metal substrate, so as to make a polymer,
   wherein the monomer is chemically and directly coupled onto the surface of the metal substrate through oxygen atoms, and the polymerization is generated through a ring-opening polymerization or dehydration-polymerization of the monomer with a catalyst, wherein the polymer is at least one selected from the group consisting of polyglycolic acid, poly-L-lactic acid, poly-D,L- lactic acid, polylactic-co-glycolic acid, poly-ϵ-carprolactone, poly(trimethylene carbonate), poly-p-dioxanone, polyaminoic acid, polyanhydride, polyorthoester and copolymers thereof.

* * * * *